United States Patent
Onda

(10) Patent No.: US 9,974,434 B2
(45) Date of Patent: May 22, 2018

(54) OPHTHALMIC IMAGING APPARATUS AND IMAGE GENERATION METHOD THEREFOR

(71) Applicant: CANON KABUSHIKI KAISHA, Tokyo (JP)

(72) Inventor: Suguru Onda, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 135 days.

(21) Appl. No.: 15/188,495

(22) Filed: Jun. 21, 2016

(65) Prior Publication Data

US 2016/0374548 A1 Dec. 29, 2016

(30) Foreign Application Priority Data

Jun. 23, 2015 (JP) ................. 2015-125839

(51) Int. Cl.
*A61B 3/00* (2006.01)
*G06T 7/00* (2017.01)
(Continued)

(52) U.S. Cl.
CPC .......... *A61B 3/0025* (2013.01); *A61B 3/1015* (2013.01); *A61B 3/1025* (2013.01);
(Continued)

(58) Field of Classification Search
CPC ... A61B 3/0025; A61B 3/1015; A61B 3/1025; A61B 3/113; A61B 3/1225; A61B 3/145;
(Continued)

(56) References Cited

U.S. PATENT DOCUMENTS

2001/0026584 A1* 10/2001 Sommer ............... H04L 1/0047
375/233
2004/0119892 A1* 6/2004 Ishihara ................ H04N 9/78
348/663
(Continued)

FOREIGN PATENT DOCUMENTS

| JP | 2000-039560 A | 2/2000 |
|---|---|---|
| JP | 2012-255978 A | 12/2012 |
| JP | 2014-68703 A | 4/2014 |

*Primary Examiner* — Edward Park
(74) *Attorney, Agent, or Firm* — Canon USA Inc., IP Division

(57) ABSTRACT

A processor extracts a reference signal of a scanner included in an adaptive optics SLO apparatus output while the scanner performs reciprocating scanning once on a region of an eye, generates sampling data strings of reciprocating scanning based on an electric signal obtained by a photo-electric conversion unit included in the adaptive optics SLO apparatus using the reference signal as a sampling reference position, and compares, among the sampling data strings of the reciprocating scanning, a sampling data string of forward scanning with a sampling data string of backward scanning so as to evaluate the correlation between the sampling data strings, and compensates a sampling reference position based on a result of the evaluation. An image construction unit assembles image data to construct an image of the region of the eye based on the sampling data strings of the reciprocating scanning in accordance with the compensated sampling reference position.

17 Claims, 7 Drawing Sheets

(51) Int. Cl.
*A61B 3/14* (2006.01)
*G02B 27/00* (2006.01)
*A61B 3/113* (2006.01)
*A61B 3/10* (2006.01)
*A61B 3/12* (2006.01)
*G06T 7/73* (2017.01)
*G06T 7/246* (2017.01)

(52) U.S. Cl.
CPC ............ *A61B 3/113* (2013.01); *A61B 3/1225* (2013.01); *A61B 3/145* (2013.01); *G02B 27/0031* (2013.01); *G02B 27/0068* (2013.01); *G06T 7/0014* (2013.01); *G06T 7/248* (2017.01); *G06T 7/74* (2017.01); *G06T 2207/20056* (2013.01); *G06T 2207/30041* (2013.01)

(58) Field of Classification Search
CPC ............ G02B 27/0031; G02B 27/0068; G06T 7/0014; G06T 2207/20056; G06T 2207/30041
See application file for complete search history.

(56) References Cited

U.S. PATENT DOCUMENTS

| | | | |
|---|---|---|---|
| 2009/0231721 A1* | 9/2009 | Kajita | G02B 26/0833 359/630 |
| 2011/0317228 A1* | 12/2011 | Matsuo | H04N 1/047 358/480 |
| 2016/0374548 A1* | 12/2016 | Onda | A61B 3/0025 351/206 |

* cited by examiner

OPHTHALMIC IMAGING APPARATUS AND IMAGE GENERATION METHOD THEREFOR

BACKGROUND OF THE INVENTION

Field of the Invention

The present invention generally relates to ophthalmic imaging, and in particular it relates an image generation apparatus and an image generation method for generating an image of a certain region of an eye to be inspected.

Description of Related Art

Inspection of a fundus of an eye is conventionally performed for early diagnosis of lifestyle-related diseases and diseases that are causes of blindness. A scanning laser ophthalmoscope (SLO) is an ophthalmic apparatus utilizing a confocal laser microscope principle. The SLO apparatus performs high-speed raster scan on a fundus of an eye to be inspected, by using laser light which is measurement light incident on the fundus, and obtains a fundus image of high resolution which is a plane image from intensity of return light which is light scattered by the fundus.

In recent years, an adaptive optics SLO (AO-SLO) apparatus has been developed. The OA-SLO apparatus includes an adaptive optics system which measures, in real time, aberration of an eye to be inspected, by using a wavefront sensor, and compensates the aberration of measurement light and return light which occurs in the eye to be inspected, by using a wavefront compensation device. This adaptive optics SLO apparatus is capable of obtaining a plane image of high transverse resolution (hereinafter referred to as an "AO-SLO image" where appropriate).

Such an apparatus which obtains a fundus image performs 2D scanning using measurement light from a resonant scanner or a galvanoscanner. Furthermore, a control circuit of such a scanner, for example, generates a synchronizing signal for image generation in synchronization with scanning of the scanner so as to generate an image from a detection signal detected by a photodetector. Then, a fundus image is formed by matching or synchronizing the signal indicating an optical scanning position of the scanner and an electric sampling position of the photodetector.

However, due to fluctuation of frequency of the resonant scanner, time delay of an electric circuit system, or the like, an optical scanning position of the scanner obtained from the synchronizing signal tends to mismatch the electric sampling position of the photodetector. Furthermore, since the adaptive optics SLO has high resolution, a difference between the optical scanning position of the scanner and the electric sampling position of the photodetector considerably affects the adaptive optics SLO. Accordingly, a large positional shift occurs between images of consecutive optical scan lines which are sampled in accordance with the synchronizing signal, and accordingly degradation of image quality, such as distortion of an image, tends to occur.

To address these disadvantages, Japanese Patent Laid-Open No. 2000-39560 discloses a method for obtaining or controlling an accurate position of scanning of the scanner using a dedicated hardware configuration. Furthermore, Japanese Patent Laid-Open No. 2012-255978 discloses a method for performing control such that only signals in positions corresponding to pixels of an image are obtained by outputting a sampling clock corresponding to a scanner signal. However, also in this method, a hardware configuration for accurately detecting a scanner position is required. Furthermore, Japanese Patent Laid-Open No. 2014-68703 discloses a method for capturing a chart image for image compensation before imaging, obtaining distortion of an image from the captured image in advance, and compensating the distortion by an image process.

As the resolution of an AO-SLO image becomes higher, an angle of view becomes larger, and a frame rate becomes higher, a positional shift between images of consecutive optical scan lines becomes increasingly more relevant even if a shift between the optical scanning position and the electric sampling position is considerably small. In this case, even if the hardware configuration for detecting a scanner position is employed, as disclosed in Japanese Patent Laid-Open No. 2000-39560 and Japanese Patent Laid-Open No. 2012-255978, it becomes considerably more difficult to detect a small shift between the optical scanning position and the electric sampling position with high accuracy and appropriate responsivity. Furthermore, when the method for adding a special hardware is employed, as disclosed in Japanese Patent Laid-Open No. 2000-39560 and Japanese Patent Laid-Open No. 2012-255978, an increased cost may be required for fabricating the apparatus. Furthermore, the methods for adding a special hardware, as disclosed in Japanese Patent Laid-Open No. 2000-39560 and Japanese Patent Laid-Open No. 2012-255978, adversely affect a size of the apparatus, restrict design, or adversely affect the number of assembly operations due to an increase in the number of components.

Furthermore, as for the shift between the optical scanning position and the electric sampling position, an amount of the shift may be changed in each imaging operation since the shift is affected by temperature in the apparatus, instability of a power source, and the like. Therefore, as described in Japanese Patent Laid-Open No. 2014-68703, even if distortion compensation is performed by an image process by obtaining a chart image for image compensation before image capturing so that image distortion is obtained in advance, distortion occurs in a captured image again and degradation of image quality occurs. In particular, in the case of ophthalmic apparatuses, it is difficult to simultaneously capture a chart image for image compensation and a fundus image using measurement light from the single resonant scanner in terms of a configuration of the apparatus, and therefore, it is difficult to compensate the entire distortion in an image using the method disclosed in Japanese Patent Laid-Open No. 2014-68703.

Specifically, in conventional techniques, it is difficult to obtain an image in which distortions caused by characteristics of a scanner are compensated without using a special hardware configuration, a chart image for image compensation, or the like.

SUMMARY OF THE INVENTION

The various aspects of the present invention provide an image generation apparatus and an image generation method capable of obtaining an image in which distortion thereof caused by characteristics of a scanner is compensated without using a special hardware configuration, a chart image for image compensation, or the like.

According to an aspect of the present invention, an image generation apparatus is connected to an ophthalmic apparatus including a photoelectric conversion unit which receives return light of measurement light used by a scanner to scan a region of an eye to be inspected and converts the return light into an electric signal. The image generation apparatus includes an extraction unit configured to extract a reference signal of the scanner obtained while the scanner performs reciprocating scanning once, a data string generation unit configured to generate sampling data strings of reciprocating scanning based on the electric signal using the reference signal as a sampling reference position, an evaluation unit configured to compare, among the sampling data strings of the reciprocating scanning, a sampling data string of forward scanning with a sampling data string of backward scanning using a spatial frequency region of the sampling data string of the forward scanning and a spatial frequency region of the sampling data string of the forward scanning so as to evaluate the correlation between the sampling data strings, a reference position compensation unit configured to compensate the sampling reference position in accordance with a result of the evaluation performed by the evaluation unit, and an image construction unit configured to assemble image data to construct an image of the region of the eye based on the sampling data strings of the reciprocating scanning in accordance with the sampling reference position compensated by the reference position compensation unit.

Further features of the present invention will become apparent from the following description of exemplary embodiments with reference to the attached drawings.

DESCRIPTION OF THE EMBODIMENTS

Hereinafter, an embodiment of the present invention will be described with reference to the accompanying drawings.

In the embodiment of the present invention, a case where, when an image of a retina (a fundus) is captured as a certain region of an eye to be inspected by an adaptive optics SLO apparatus, the image is configured based on a signal value obtained by scanning performed on the certain region using a resonant scanner and a galvanoscanner will be described.

In particular, an image generation apparatus of this embodiment obtains a group of trigger signals of the galvanoscanner corresponding to one image in a horizontal direction of the image and a group of trigger signals of the resonant scanner corresponding to two lines of reciprocating scanning in a vertical direction of the image. Then the image generation apparatus of this embodiment generates sampling data strings of reciprocating scanning using a scanner position estimated from a timing of output of such a trigger signal as a sampling reference position. The image generation apparatus of this embodiment calculates a sampling reference position in which an amount of shift between a sampling data string of forward scanning and a sampling data string of backward scanning in the sampling data strings of the reciprocating scanning is smallest for each reciprocating scanning. The image generation apparatus of this embodiment compensates a shift among the sampling reference positions due to variation of a frequency of the resonant scanner or a time delay of an electric circuit system. The image generation apparatus of this embodiment obtains an actual scanner position at a time of output of a trigger signal of the resonant scanner in accordance with the compensated sampling reference position so as to generate image data corresponding to the sampling data strings of the reciprocating scanning. By this, in this embodiment, an image of a retina (a fundus image) in which image distortion caused by characteristics of a scanner (the resonant scanner in this embodiment) is compensated may be obtained without using a special hardware configuration, a chart image for image compensation, or the like.

Schematic Configuration of Image Generation Apparatus

Figure 1:
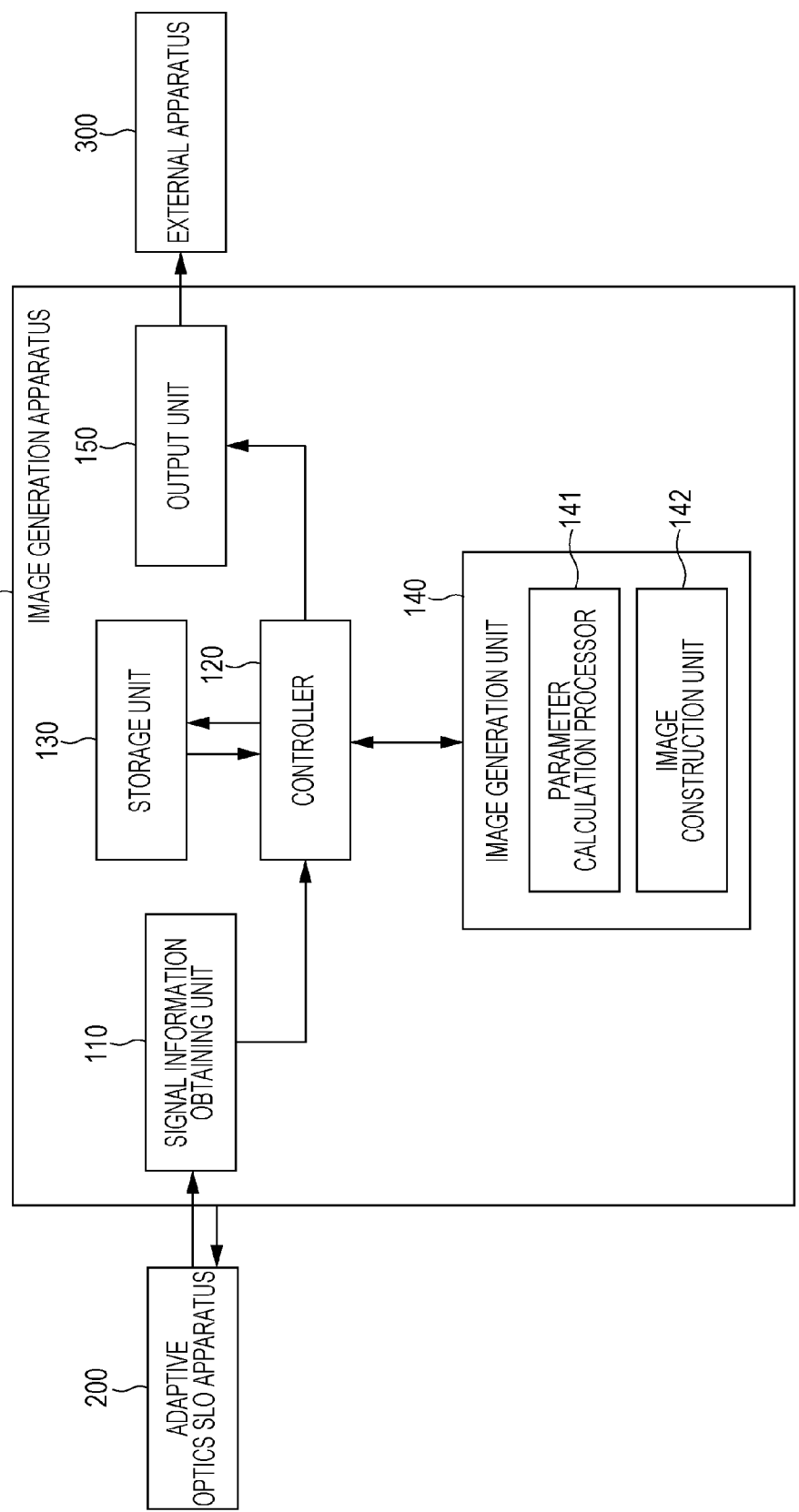
FIG. 1 is a block diagram schematically illustrating a configuration of an image generation system including an image generation apparatus according to an embodiment of the present invention.

FIG. 1 is a block diagram schematically illustrating a configuration of an image generation system 10 including an image generation apparatus 100 according to this embodiment of the present invention.

The image generation system 10 includes the image generation apparatus 100, an adaptive optics SLO apparatus 200, and an external apparatus 300 as illustrated in FIG. 1.

The adaptive optics SLO apparatus 200 (an ophthalmic apparatus) includes a photoelectric conversion unit which receives return light of measurement light used for reciprocating scanning performed by a scanner on a retina (a fundus) which is a certain region of an eye to be inspected, and converts the return light into an electric signal. The image generation apparatus 100 is connected to (and communicates with) the adaptive optics SLO apparatus 200 in a known manner. The image generation apparatus 100 includes a signal information obtaining unit 110, a controller 120, a storage unit 130, an image generation unit 140, and an output unit 150 as illustrated in FIG. 1.

The signal information obtaining unit 110 obtains trigger signals of a resonant scanner and a galvanoscanner, and signal information such as a signal of reflection from a retina of the eye to be inspected, from the adaptive optics SLO apparatus 200. Here, the trigger signal is a reference signal indicating that the resonant scanner and the galvanoscanner are in specific positions (reference positions). The signal information obtained by the signal information obtaining unit 110 is stored in the storage unit 130 through the controller 120.

The controller 120 integrally controls operations of the units of the image generation apparatus 100.

The storage unit 130 is a computer hardware device that stores the signal information obtained by the signal information obtaining unit 110, various information required for a process to be performed by the image generation apparatus 100, various information (including various image data) obtained in the process performed by the image generation apparatus 100, and the like. The storage unit 130 may be implemented in various ways, for example, nonvolatile random access memory.

The image generation unit 140 performs generation of various image data, and as illustrated in FIG. 1, the image generation unit 140 includes a parameter calculation processor 141 and an image construction unit 142.

The parameter calculation processor 141 extracts the trigger signals (the reference signals) of the galvanoscanner and the resonant scanner in accordance with the signal information obtained by the signal information obtaining unit 110. Specifically, in this embodiment, reference signals of the scanners output while the scanners perform reciprocating scanning once are extracted. The parameter calculation processor 141 which performs the extraction of the reference signals constitutes an extraction unit. Subsequently, the parameter calculation processor 141 generates sampling data strings corresponding to reciprocating scanning based on reflection signals (electric signals obtained by photoelectric conversion units of the adaptive optics SLO apparatus 200) using the extracted trigger signals (the reference signals) as sampling reference positions. The parameter calculation processor 141 which generates the sampling data strings constitutes a data string generation unit. Then the parameter calculation processor 141 compares sampling data strings corresponding to forward scanning with sampling data strings corresponding to backward scanning in the generated sampling data strings of the reciprocating scanning using spatial frequency regions of the sampling data strings of the forward scanning and the backward scanning and evaluates the correlations between the sampling data strings of the forward scanning and the backward scanning. The parameter calculation processor 141 which evaluates the correlations constitutes an evaluation unit. Subsequently, the parameter calculation processor 141 compensates the sampling reference positions described above in accordance with results of the evaluation. The parameter calculation processor 141 which compensates the sampling reference positions constitutes a reference position compensation unit.

The image construction unit 142 assembles image data sets to construct (form) an image of the retina of the eye to be inspected in accordance with the sampling data strings of the reciprocating scanning described above in accordance with the sampling reference positions compensated by the parameter calculation processor 141.

The output unit 150 outputs the image data generated by the image generation unit 140 and the various information and the like stored in the storage unit 130 to the external apparatus 300.

The adaptive optics SLO apparatus 200 further includes an adaptive optics system which compensates aberration of the measurement light or the return light of the measurement light which occurs in the eye to be inspected.

The external apparatus 300 is connected to (and communicates with) the image generation apparatus 100 in a known manner, and is an output/output apparatus, such as a display apparatus, or a database.

Schematic Configuration of Adaptive Optics SLO Apparatus

Next, a schematic configuration of the adaptive optics SLO apparatus 200 illustrated in FIG. 1 will be described.

Figure 2:
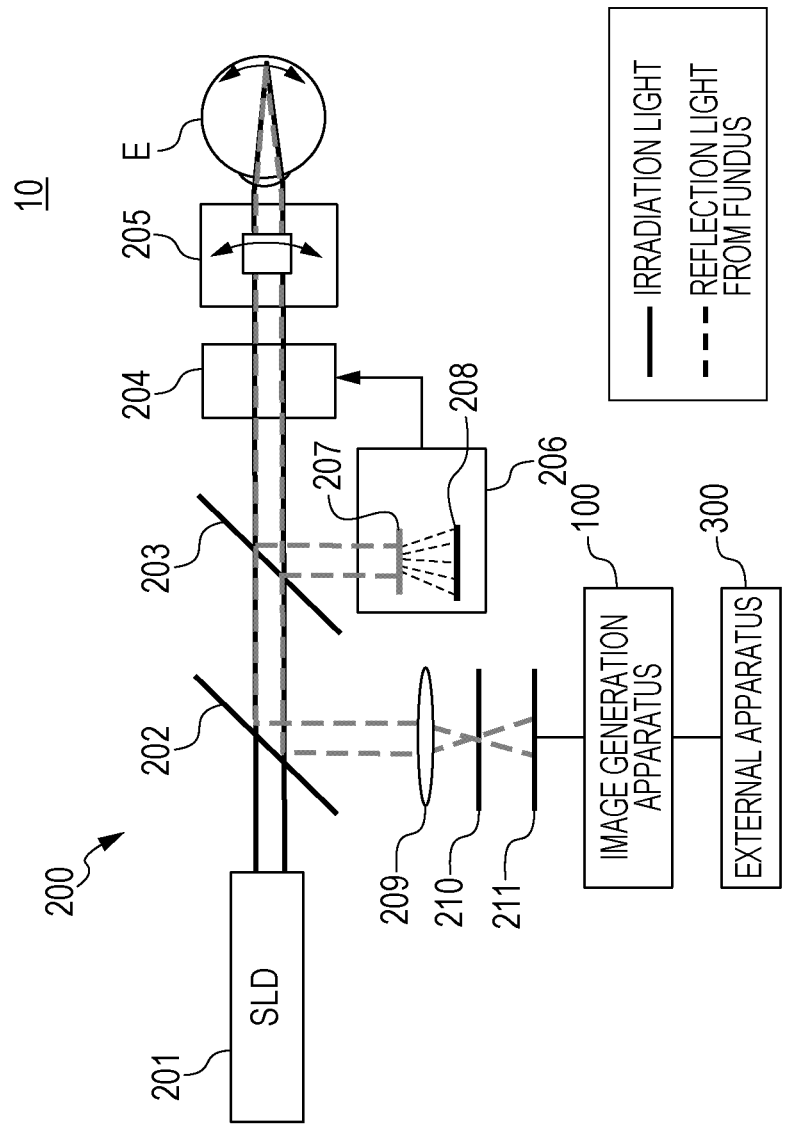
FIG. 2 is a block diagram schematically illustrating a configuration of an adaptive optics SLO apparatus illustrated in FIG. 1.

FIG. 2 is a block diagram schematically illustrating a configuration of the adaptive optics SLO apparatus 200 illustrated in FIG. 1. In addition to the schematic configuration of the adaptive optics SLO apparatus 200 illustrated in FIG. 1, the image generation apparatus 100 and the external apparatus 300 illustrated in FIG. 1 are also illustrated in FIG. 2.

As illustrated in FIG. 2, the adaptive optics SLO apparatus 200 includes a light source implemented by super luminescent diode (SLD) 201, beam splitters 202 and 203, an adaptive optics system 204, an X-Y scanning mirror 205, a Shack-Hartmann wavefront sensor 206, a focus lens 209, a diaphragm 210, and a photosensor 211.

Light emitted from the SLD 201 serving as a light source is reflected by a fundus of retina Er of an eye E to be inspected, a portion of the reflection light is guided to the Shack-Hartmann wavefront sensor 206 through the beam splitter 203, and the other portion of the reflection light is guided to the photosensor 211 through the beam splitter 202.

The Shack-Hartmann wavefront sensor 206 is used to measure aberration of the eye E and includes a CCD sensor 208 and a lens array 207 disposed in front of the CCD sensor 208. In the Shack-Hartmann wavefront sensor 206, when incident light passes the lens array 207, a group of bright spots is projected on the CCD sensor 208, and wave aberration is measured in accordance with positional shifts among the projected bright spots.

The adaptive optics system 204 compensates the aberration by driving an aberration compensation device (not shown) in accordance with the wave aberration measured by the Shack-Hartmann wavefront sensor 206. Examples of the aberration compensation device include a deformable mirror and a spatial light phase modulator. The light which has been subjected to the aberration compensation is transmitted through the beam splitters 203 and 202, the focus lens 209, and the diaphragm 210 and is guided to the photosensor 211 serving as a photoelectric conversion unit. The light guided to the photosensor 211 is converted into an electric signal in the photosensor 211.

By driving the X-Y scanning mirror 205, a scanning position of the measurement light on the fundus Er of the eye to be inspected E may be controlled and information on an imaging target region and time (the number of frames/a frame rate) specified by an imaging practitioner in advance may be obtained. The X-Y scanning mirror 205 includes a resonant scanner in an X direction which is a main scanning direction and a galvanoscanner in a Y direction which is a sub-scanning direction. Signal information of the X-Y scanning mirror 205 is transmitted to the image generation apparatus 100 and is used when the image generation apparatus 100 generates image data (moving-image data or still-image data). Although the signal information is obtained in forward scanning and backward scanning which are main scanning of the resonant scanner so that high speed frame rate is obtained in this embodiment, the present invention is not limited to this.

To focus at a specific depth position on the fundus Er of the eye E, at least adjustment using the aberration compensation device included in the adaptive optics system 204 or adjustment by moving a focus adjustment lens (not illustrated) disposed in an optical system may be employed.

Furthermore, a movement of the eye E may be tracked (tracking) so that influence of an involuntary movement of an eye referred to as an "involuntary eye movement", an eye movement caused by defect of visual fixation, or a movement of the eye E caused by movement of an examinee is reduced. In this case, measurement of a movement of the fundus Er is performed by pattern matching in which a template image which is an image of a small region of the fundus having a feature is extracted from a generated fundus image and a portion which is the most similar to the template image is retrieved from a newly generated fundus image, or the like. Here, the controller 120 of the image generation apparatus 100 performs control for tracking the movement of the eye to be inspected E and compensating an imaging position, for example. The controller 120 which performs the control for compensating the imaging position constitutes a compensation control unit. Then the adaptive optics SLO apparatus 200 compensates the imaging position by tracking the eye E in accordance with the compensation control performed by the controller 120 of the image generation apparatus 100. Specifically, a scanner, not illustrated, is disposed in the optical system of the adaptive optics SLO apparatus 200 and a position of irradiation light follows the movement of the fundus Er measured by the scanner.

Procedure of Process of Image Generation Apparatus

Next, a procedure of a process performed by the image generation apparatus 100 according to this embodiment of the present invention will be described.

Figure 3:
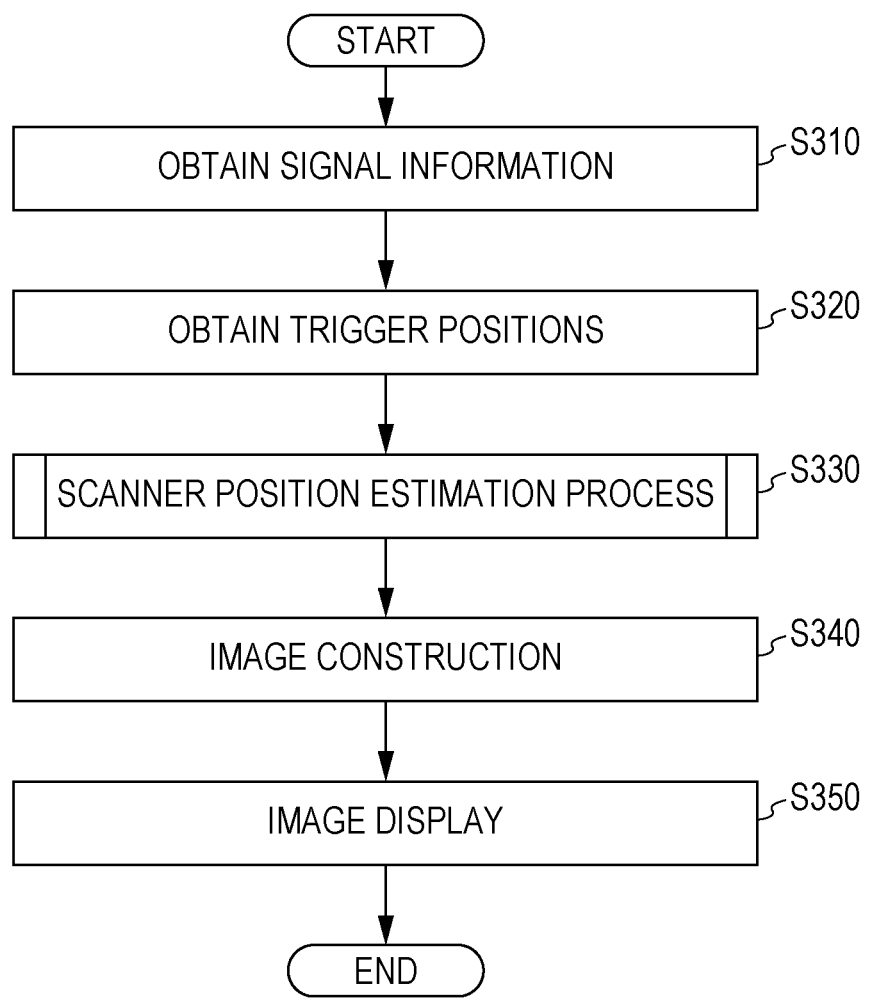
FIG. 3 is a flowchart illustrating a procedure of a process performed by the image generation apparatus according to the embodiment of the present invention.

FIG. 3 is a flowchart illustrating a procedure of a process performed by the image generation apparatus 100 according to the embodiment of the present invention.

Step S310

First, in step S310, the signal information obtaining unit 110 obtains signal information for at least one image obtained by the adaptive optics SLO apparatus 200. The signal information to be obtained includes at least three signal information items, that is, a trigger signal of the galvanoscanner and a trigger signal of the resonant scanner which are used for imaging of the retina of the eye to be inspected E, and a reflection signal which is reflected by the retina of the eye to be inspected E obtained by the imaging. The signal information obtained in step S310 is stored in the storage unit 130 through the controller 120. Furthermore, hardware control information associated with the obtained signal information is also obtained and is stored in the storage unit 130 through the controller 120. Here, the control information indicates information on a frame rate corresponding to a sampling frequency and a frequency of the galvanoscanner at a time when the reflection signal reflected by the retina of the eye E is obtained. The control information may be included in an imaging information file added to the signal information or included as tag information of the signal information.

Step S320

Subsequently, in step S320, the parameter calculation processor 141 extracts the trigger signals (the reference signals) of the galvanoscanner and the resonant scanner from the signal information stored in the storage unit 130 so as to obtain trigger positions. Here, the trigger positions serve as references for obtaining pixel values by sampling the reflection signals (the sampling reference positions). Furthermore, the parameter calculation processor 141 stores the obtained trigger position information in the storage unit 130 through the controller 120.

Figure 5:
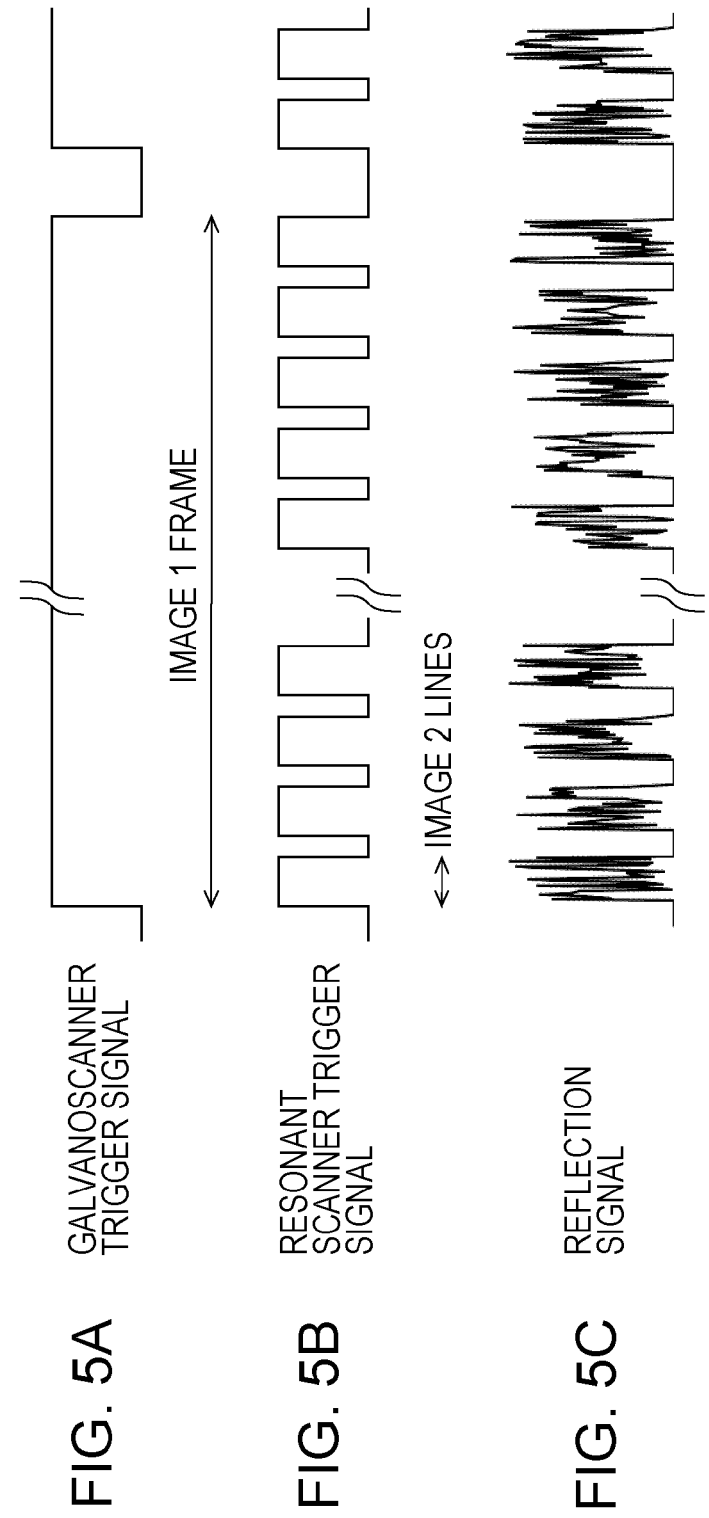
FIGS. 5A to 5C are diagrams illustrating a time chart of a trigger signal of a galvanoscanner, a time chart of a trigger signal of a resonant scanner, and a time chart of a reflection signal, respectively.

FIGS. 5A to 5C are diagrams illustrating a time chart of the trigger signal of the galvanoscanner, a time chart of the trigger signal of the resonant scanner, and a time chart of the reflection signal, respectively, according to this embodiment of the present invention.

The trigger signals of the galvanoscanner and the resonant scanner have characteristics as illustrated in FIGS. 5A and 5B, respectively, and therefore, the parameter calculation processor 141 performs extraction of the trigger signals by threshold processing. Specifically, the parameter calculation processor 141 detects and extracts a trigger signal when change of signal intensity becomes equal to or larger than a certain threshold value.

The galvanoscanner performs scanning once in a horizontal direction of an image while one trigger signal is detected and meanwhile an image is captured. The resonant scanner performs scanning for two lines (forward scanning and backward scanning) in a vertical direction of the image while one trigger signal is detected and meanwhile two lines of forward scanning and backward scanning in the vertical direction of the image are captured. Therefore, the parameter calculation processor 141 extracts a timing of start of detection of a trigger signal as a trigger position, that is, a sampling reference position.

Furthermore, the reflection signal illustrated in FIG. 5C has a value obtained by detecting intensity of reflection light from the fundus Er of the eye being inspected E using the photosensor 211 illustrated in FIG. 2. As illustrated in FIG. 5B, sampling is performed only while the trigger signal of the resonant scanner is detected, and signal information in this period is used for generation of an image.

In this embodiment, the sampling may be consecutively performed while the resonant scanner performs scanning, but the present invention is not limited to this. Furthermore, various methods may be employed as a method for obtaining a trigger position other than the method employed in this embodiment.

Step S330

Next, in step S330, the parameter calculation processor 141 generates sampling data strings for reciprocating scanning, correspond to the operation of Galvano scanner and resonant scanner, or just one of them, or to a combination of the two, based on the reflection signal in accordance with each of the trigger positions obtained in step S320. Then the parameter calculation processor 141 performs a process of estimating scanner positions (sampling reference positions) at a time of outputting the trigger signals using the generated sampling data strings. Then the parameter calculation processor 141 stores the obtained scanner position information in the storage unit 130 through the controller 120. Hereinafter, a procedure of the scanner position estimation process performed in step S330 of FIG. 3 will be described in detail with reference to FIG. 4.

Figure 4:
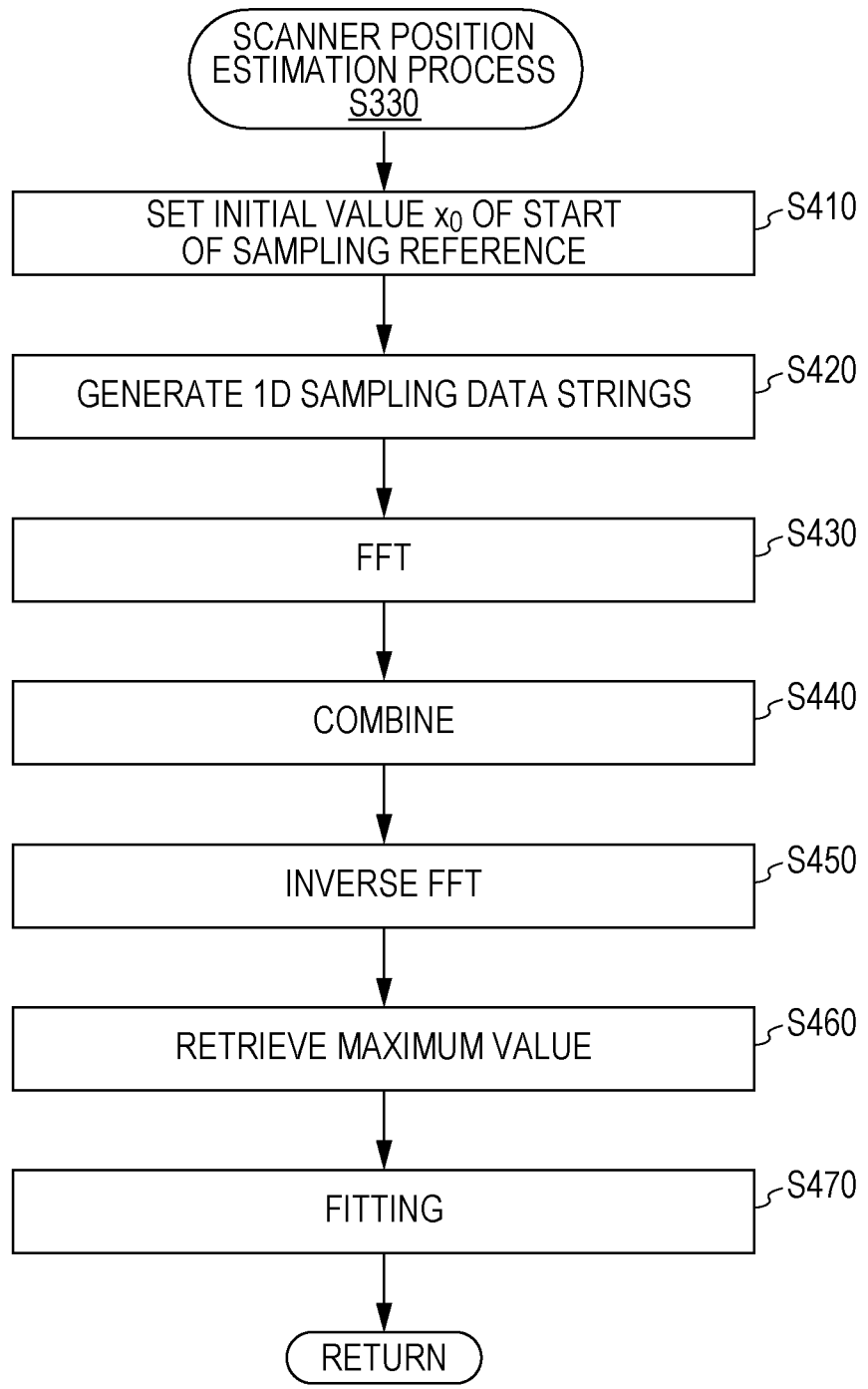
FIG. 4 is a flowchart illustrating a procedure of a scanner position estimation process in step S330 of FIG. 3 in detail.

FIG. 4 is a flowchart illustrating a procedure of the scanner position estimation process performed in step S330 of FIG. 3 in detail. Here, in a description below, the scanner position estimation process is performed for each reciprocating scanning operation of the resonant scanner on each of a plurality of images consecutively captured, and the scanner position estimation process is repeatedly performed the number of times corresponding to a number of reciprocating scanning operations performed on one image, and this process is similarly performed on the plurality of images.

In the scanner position estimation process of this embodiment, a sampling data string corresponding to forward scanning is compared with a sampling data string corresponding to backward scanning in sampling data strings of the reciprocating scanning using spatial frequency domain data regions of the sampling data string of the forward scanning and the sampling data string of the backward scanning so that the correlation between the sampling data strings is evaluated. In this embodiment, the correlation is evaluated by comparing the sampling data string of the forward scanning with the sampling data string of the backward scanning by pattern matching using a spatial frequency function of a pixel which is referred to as a "cross correlation method", for example. As concrete evaluation, a process of calculating a position in which the correlation between the sampling data string of the forward scanning and the sampling data string of the backward scanning in the reciprocating scanning is the highest is performed. Note that, although the cross correlation method is used for the evaluation in the example described above, the embodiment is not limited to this, and a phase-only-correlation method only using a phase space may be used for the evaluation.

Step S410

First, in step S410, the parameter calculation processor 141 sets a position of the resonant scanner at a time when the trigger signal is output as an initial position $x_0$ of a sampling reference start position in accordance with the control information obtained in step S310. Here, various methods may be employed for setting the initial position $x_0$, and the initial position $x_0$ is set taking a trigger delay from a trigger position into consideration, for example, in this embodiment. Furthermore, as another method, a method for narrowing, in a case where a plurality of images are to be consecutively captured, a retrieval range of an estimation position by setting an average scanner estimation position of reciprocating scanning operations performed on images captured before the images to be captured as an initial position may be employed.

Step S420

Next, in step S420, the parameter calculation processor 141 generates a pair of 1D sampling data strings corresponding to two lines for one reciprocating scanning operation of the resonant scanner in accordance with the initial position $x_0$ of the sampling reference start position set in step S410.

Step S430

Subsequently, in step S430, the parameter calculation processor 141 generates 1D spatial frequency region data strings by performing Fourier transform on the sampling data strings for the two lines of the reciprocating scanning operation generated in step S420. Here, as a method for calculating the spatial frequency region data strings, a calculation method using discrete Fourier transform may be employed, for example. In particular, a calculation method using Fast Fourier transform (FFT) is preferably employed to realize a high-speed operation. In a description below, as the method for calculating the spatial frequency region data strings, the calculation method using FFT is employed, and a Hann window which is a general window function is used.

Furthermore, a region on which FFT is to be performed preferably includes a region having luminance gradient, such as a region of some sort of structure, and therefore, the region is as large as possible and includes a region in which a speed of the resonant scanner at scanning center is high. Specifically, to include the region in which the speed of the resonant scanner at the scanning center is high corresponds to performance of the evaluation described above using the sampling data strings of the reciprocating scanning in a range which is less affected by image distortion caused by scanning of the resonant scanner than other ranges.

Note that to realize higher speed calculation, only a narrower region including a region having large luminance gradient in a sampling data string may be used or an amount of calculation may be reduced by FFT using a fixed point, bit shift, or the like. As described above, the method for the calculation of the spatial frequency region is not limited to the methods described above. Furthermore, in this embodiment, a mode in which the evaluation described above is performed on a region in which at least change of luminance gradient is large in the sampling data string of the forward scanning and the sampling data string of the backward scanning which are adjacent to each other may be employed.

Step S440

Subsequently, in step S440, the parameter calculation processor 141 combines a spatial frequency region data string A of the sampling data string of the forward scanning generated in step S430 and a spatial frequency region data array B of the sampling data string of the backward scanning generated in step S430 with each other. Here, as a method for the combining, a general method used in a calculation in the cross correlation method is used, and A is multiplied by conjugation of B.

Step S450

Thereafter, in step S450, the parameter calculation processor 141 performs inverse Fourier transform on the combined image of the spatial frequency region data strings of the sampling data strings of the reciprocating scanning obtained in step S440. The inverse FFT is used also here as the inverse Fourier transform.

Step S460

Subsequently, in step S460, the parameter calculation processor 141 retrieves a position of a data point having the maximum value in the inverse FFT data string obtained in step S450.

Figure 6:
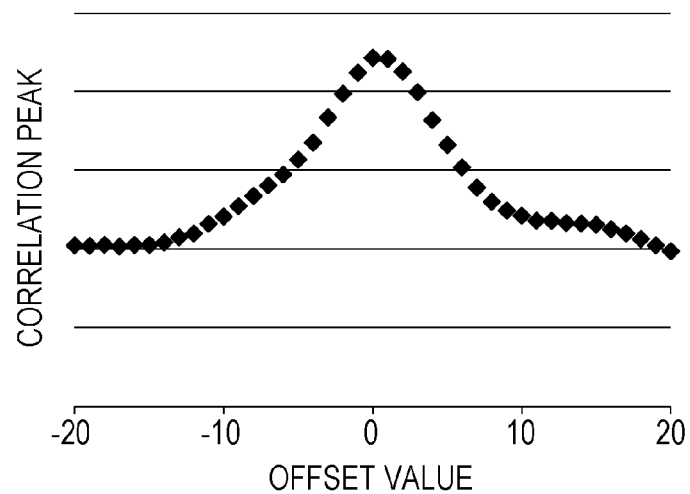
FIG. 6 is a graph illustrating inverse FFT data array obtained by an inverse FFT process in step S450 of FIG. 4.

FIG. 6 is a graph illustrating an inverse FFT data string obtained by the inverse FFT process performed in step S450 of FIG. 4. In the graph of FIG. 6, an axis of ordinates indicates a magnitude of a correlation peak, and an axis of abscissae indicates an offset value of the sampling lines in the reciprocating scanning in a scanning direction. The offset value indicates the amount of shift (offset) between forward and backward scanning signals with respect to certain reference. According to the graph of FIG. 6, the maximum value is obtained when the offset value is 0. The 0 indicates a situation where the forward and backward scanning signals have not shift. Here, as a method for retrieving a data point having the maximum value, retrieval may be performed only in a range of a physically possible minimum shift, due to events such as delay of a frequency of the resonant scanner or latency an electric circuit, and any other method may be employed.

Since the cross correlation method is used when the evaluation described above is performed in this embodiment, a mode for retrieving the maximum value of the correlation peak may be employed, for example. Furthermore, also in a case where a phase-only-correlation method is used when the evaluation described above is performed, the maximum value of the correlation peak may be retrieved, for example.

Step S470

Then, in step S470, the parameter calculation processor 141 performs fitting using data in the vicinity of the position of the data point obtained in step S460 so as to calculate a maximum peak value in inverse FFT data and an offset value corresponding to the maximum peak value.

Since the cross correlation method is used when the evaluation described above is performed in this embodiment, a mode for determining a position of a correlation peak by performing arbitrary fitting in the vicinity of the maximum value of the correlation peak may be employed. Furthermore, also in a case where the phase-only-correlation method is used when the evaluation described above is performed, the mode for determining a position of a correlation peak by performing arbitrary fitting in the vicinity of the maximum value of the correlation peak may be employed.

By performing the fitting as described above, a reference position may be obtained in each sub-sampling unit. Although an arbitrary least-square method may be used for the fitting, parabola fitting employing easy calculation is used in this embodiment. In FIG. 6, by performing the parabola fitting using data in three points having offset values of −1, 0, and 1, an offset value having the highest correlation between the sampling data strings in the reciprocating scanning may be calculated in a sub-sampling unit. By taking a trajectory of the resonant scanner into consideration for the calculated offset value, a shift amount $\Delta x$ from the sampling reference start position may be calculated and "$x_0 + \Delta x$" may be determined as the compensated sampling reference position which is a position of the resonant scanner at the time when the trigger signal is output. The compensated sampling reference position information is transmitted from the parameter calculation processor 141 and stored in the storage unit 130 through the controller 120.

The scanner position estimation process in step S330 of FIG. 3 is executed by performing the process from step S410 to step S470 of FIG. 4. Here, FIG. 3 is referred to again.

Step S340

After the process in step S330 of FIG. 3 is terminated according to FIG. 4, the process proceeds to step S340.

In step S340, the image construction unit 142 assembles image data to construct an image of the retina of the eye to be inspected based on the sampling data strings of the reciprocating scanning described above in accordance with the sampling reference position (the sampling reference position compensated by the parameter calculation processor 141) obtained in step S330. Specifically, the image construction unit 142 assembles image data by performing sine compensation for two lines of the image corresponding to one reciprocating scanning operation of the resonant scanner. The assembling of the image data is performed to address image distortion by performing weighting on the number of samplings of each pixel by approximating a scanning trajectory of the resonant scanner to a sine wave since an image is distorted when data is uniformly divided into positions in a direction of the axis of ordinates due to inconstant scanning speed of the resonant scanner. The image construction unit 142 stores the assembled image data in the storage unit 130 through the controller 120.

Figure 7:
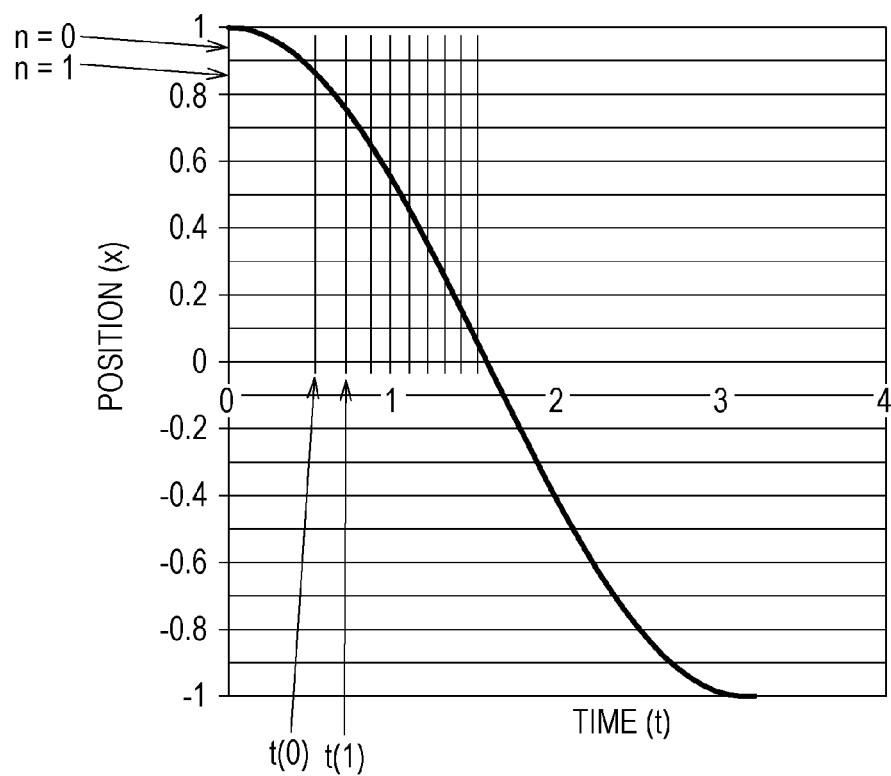
FIG. 7 is a diagram illustrating sine compensation performed when an image construction process in step S340 of FIG. 3 is performed.

FIG. 7 is a diagram illustrating sine compensation performed when the image construction process in step S340 of FIG. 3 is performed. In FIG. 7, an axis of abscissae indicates a time t, an axis of ordinates indicates a position x, and it is assumed that a scanning trajectory of the resonant scanner corresponds to a sine wave of the frequency trigger signal of the resonant scanner obtained in step S310 and amplitude is 1.0. The sine wave of FIG. 7 is divided into 10 sections along the axis of ordinates, and n=0 to n=9 are assigned to the divided sections from a time point 0.0. Furthermore, t(0), t(1), and so on are assigned to time points of intersections between straight lines obtained by the division along the axis of ordinates and the sine wave. Data sampled while the resonant scanner scans the sections obtained by the division along the axis of ordinates is assigned to pixels in corresponding positions. By this, although the sampling is performed in several tens MHz at even time interval, different periods of time in which the resonant scanner scans the individual sections, that is, the resonant scanner performs the sampling, are required for different pixels. Therefore, in a case where an obtained luminance value of a reflection signal is associated with a pixel value in a corresponding position and a plurality of signals correspond to one pixel, a value of the pixel is obtained as an average value of the plurality of signals. Although the scanning trajectory of the resonant scanner is approximated to the sine wave in this embodiment, the approximating method is not limited to this.

Here, the forming of an image (image construction) is performed on individual images which are consecutively captured. Specifically, the process described above is performed on one image corresponding to one trigger signal of the galvanoscanner obtained in step S320 and this operation is repeatedly performed for a number of several images. After the image construction is performed for all images, an image group to be stored in the storage unit 130 is generated by integrating the images.

Figure 8A:
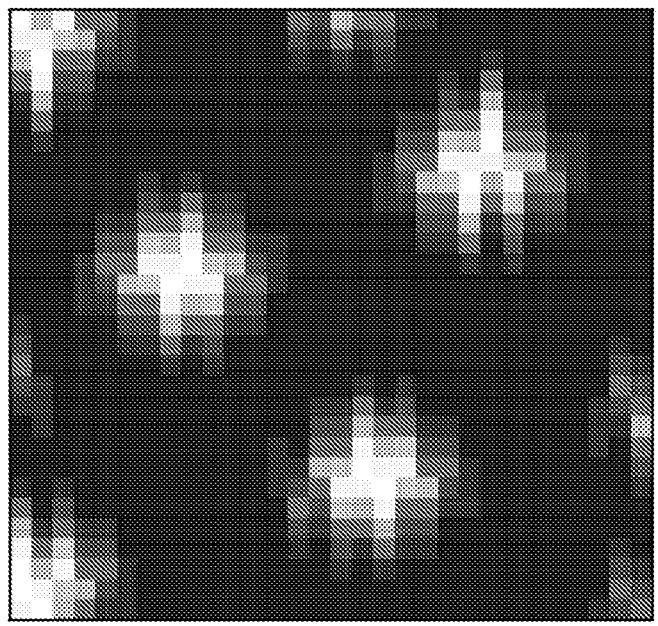
FIGS. 8A and 8B are diagrams illustrating captured images of a photoreceptor cell in a fundus of an eye to be inspected.
Figure 8B:
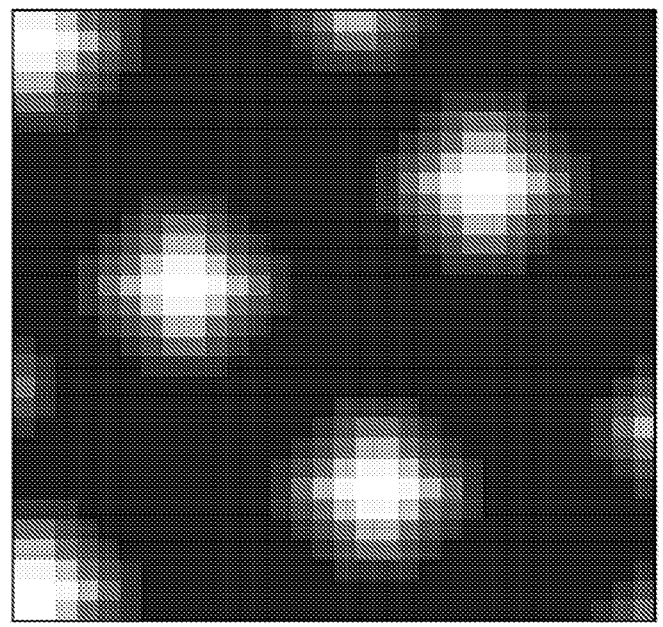

FIGS. 8A and 8B are diagrams illustrating images of a photoreceptor cell in the fundus Er of the eye to be inspected according to this embodiment of the present invention. In a case where the sampling reference position is shifted from an actual position of the resonant scanner, an amount of shift between pixels which are adjacent to each other in the horizontal direction is large as illustrated in FIG. 8A, and accordingly, degradation of image quality occurs. On the other hand, in a case where a scanner position is estimated in step S330 and the sampling reference position is appropriately compensated, an amount of shift between pixels which are adjacent to each other in the horizontal direction is considerably small as illustrated in FIG. 8B, and an image in which distortion thereof is compensated may be generated.

Step S350

Next, in step S350, the output unit 150 outputs image data of the retina obtained in step S340 to the external apparatus 300. By this, an image based on the image data output from the output unit 150, for example, is displayed in the external apparatus 300 for the examiner or the like. Furthermore, the output unit 150 outputs information on the image construction, such as sampling reference positions of individual reciprocating scanning operations of the scanner stored in the storage unit 130 in step S310 to step S330, to the external apparatus 300 (a database, for example).

When the process in step S350 is terminated, the process of the flowchart illustrated in FIG. 3 is terminated.

Note that, in this embodiment, the evaluation described above may be performed on individual 1D sampling data strings corresponding to a forward scanning and a backward scanning which are adjacent to each other or may be performed on individual 2D sampling data strings corresponding to a plurality of reciprocating scanning operations.

According to this embodiment, an image in which distortion thereof caused by characteristics of a scanner is compensated without using a special hardware configuration, a chart image for compensation, or the like may be obtained.

Other Embodiments

In the foregoing embodiment of the present invention, a position of the resonant scanner at a time when a trigger signal is output is estimated every two lines of an image corresponding to reciprocating scanning of the resonant scanner. This is because the adaptive optics SLO apparatus 200 has high transverse resolution, and therefore, a small error of the scanner position caused by a scanner frequency and a time delay of an electric circuit system causes uneven image distortion in individual reciprocating scanning operations. This is further because variation of the scanning of the resonant scanner is affected by temperature in a body of the adaptive optics SLO apparatus 200, instability of a power source, and the like, and therefore, variation of an error of the scanner position is large. The image distortion may appear in a certain cycle depending on a setting of the scanner of the adaptive optics SLO apparatus 200, an imaging condition of an obtained image, or a used scanner (such as a polygonal mirror) other than the resonance scanner. In this case, the number of estimation steps may be reduced by estimating the scanner positions in individual reciprocating scanning operations corresponding to the number of cycles in which image distortion appears.

The estimation of the scanner position may not be performed for one reciprocating scanning line but may be simultaneously performed on a plurality of reciprocating scanning lines. Specifically, a plurality of forward scanning lines and backward scanning lines are set as 2D images, and comparison between spatial frequency regions by 2D FFT is performed so that a positional shift in a scanning direction is calculated. By this method, a uniform sampling reference position may be calculated at once.

Furthermore, improvement of image quality of an image to be displayed and improvement of accuracy of image calculation are expected when an image in which distortion is compensated is used, and therefore, the compensation of distortion of an image of the foregoing embodiment which is executed immediately after imaging in a quick manner may be realized by a hardware configuration and parallel calculation. For example, a multicore calculator, such as an arbitrary FPGA or a GPU, or the like is additionally provided and the calculation to be performed by the image generation unit 140 may be performed by a pipeline process for a plurality of reciprocating scanning operations in parallel.

Moreover, although the retina (the fundus Er) of the eye to be inspected E is employed as the certain region of the eye to be inspected to be subjected to the reciprocating scanning performed by the scanner in the foregoing embodiment of the present invention, the present invention is not limited to this and other portions of the eye to be inspected E may be employed.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-125839, filed Jun. 23, 2015, which is hereby incorporated by reference herein in its entirety.

What is claimed is:

1. An image generation apparatus connected to an ophthalmic apparatus including a photoelectric conversion unit which receives return light of measurement light used by a scanner to scan a region of an eye to be inspected and converts the return light into an electric signal, the image generation apparatus comprising:
   an extraction unit configured to extract a reference signal of the scanner obtained while the scanner performs reciprocating scanning once;
   a data string generation unit configured to generate sampling data strings of reciprocating scanning based on the electric signal using the reference signal as a sampling reference position;
   an evaluation unit configured to compare, among the sampling data strings of the reciprocating scanning, a sampling data string of forward scanning with a sampling data string of backward scanning using a spatial frequency region of the sampling data string of the forward scanning and a spatial frequency region of the sampling data string of the backward scanning so as to evaluate the correlation between the sampling data strings;
   a reference position compensation unit configured to compensate the sampling reference position in accordance with a result of the evaluation performed by the evaluation unit; and
   an image construction unit configured to assemble image data to construct an image of the region of the eye based on the sampling data strings of the reciprocating scanning in accordance with the sampling reference position compensated by the reference position compensation unit.

2. The image generation apparatus according to claim 1, wherein the ophthalmic apparatus further includes an adaptive optics system which compensates aberration of the measurement light and/or the return light occurred in the eye.

3. The image generation apparatus according to claim 1, further comprising a compensation control unit configured to control compensation of an imaging position by tracking a movement of the eye.

4. The image generation apparatus according to claim 1, wherein the evaluation unit performs the evaluation on a range in which at least change of luminance gradient is large in the sampling data string of the forward scanning and the sampling data string of the backward scanning.

5. The image generation apparatus according to claim 1, wherein the spatial frequency regions are calculated using discrete Fourier transform.

6. The image generation apparatus according to claim 1, wherein the spatial frequency regions are calculated using fast Fourier transform.

7. The image generation apparatus according to claim 1, wherein the evaluation unit performs the evaluation on individual 1D sampling data strings corresponding to the forward scanning and the backward scanning which are adjacent to each other.

8. The image generation apparatus according to claim 1, wherein the evaluation unit performs the evaluation on individual 2D sampling data strings corresponding to a plurality of reciprocating scanning operations.

9. The image generation apparatus according to claim 1, wherein the evaluation unit performs the evaluation using a cross correlation method.

10. The image generation apparatus according to claim 9, wherein the evaluation unit retrieves a maximum value of a correlation peak according to the cross correlation method.

11. The image generation apparatus according to claim 9, wherein the evaluation unit determines a position of a correlation peak by arbitrary fitting in the vicinity of a maximum value of the correlation peak according to the cross correlation method.

12. The image generation apparatus according to claim 1, wherein the evaluation unit performs the evaluation using a phase-only correlation method.

13. The image generation apparatus according to claim 12, wherein the evaluation unit retrieves a maximum value of a correlation peak according to the phase-only correlation method.

14. The image generation apparatus according to claim 12, wherein the evaluation unit determines a position of a correlation peak by arbitrary fitting in the vicinity of a maximum value of the correlation peak according to the phase-only correlation method.

15. The image generation apparatus according to claim 1, wherein the evaluation unit performs the evaluation by performing pattern matching.

16. An image generation method of an ophthalmic apparatus including a photoelectric conversion unit which receives return light of measurement light used by a scanner to scan a region of an eye to be inspected and converts the return light into an electric signal, the image generation method comprising:

extracting a reference signal of the scanner obtained while the scanner performs reciprocating scanning once;

generating sampling data strings of reciprocating scanning based on the electric signal using the reference signal as a sampling reference position;

comparing, among the sampling data strings of the reciprocating scanning, a sampling data string of forward scanning with a sampling data string of backward scanning using a spatial frequency region of the sampling data string of the forward scanning and a spatial frequency region of the sampling data string of the backward scanning so as to evaluate a correlation between the sampling data strings;

compensating the sampling reference position in accordance with a result of the evaluation; and assembling image data to construct an image of the region of the eye based on the sampling data strings of the reciprocating scanning in accordance with the compensated sampling reference position.

17. A non-transitory computer-readable storage medium which stores a program for executing the image generation method set forth in claim 16 by a computer.

* * * * *